United States Patent [19]

Chaudhuri et al.

[11] Patent Number: 5,385,948
[45] Date of Patent: Jan. 31, 1995

[54] ALKOXYALKYL LACTAMS AS SOLVENTS FOR MACRO AND MICROEMULSIONS

[75] Inventors: Ratan K. Chaudhuri, Butler; Kolazi S. Narayanan, Palisades Park; Lowell R. Anderson, Morristown, all of N.J.

[73] Assignee: ISP Investments Inc., Wilmington, Del.

[21] Appl. No.: 17,914

[22] Filed: Feb. 16, 1993

[51] Int. Cl.[6] .................... A01N 25/00; A01N 43/00; A01N 33/00
[52] U.S. Cl. ................................. 514/788; 504/234; 504/261; 504/347; 514/255; 514/506; 514/531; 540/531; 546/243; 548/551
[58] Field of Search ............... 548/551; 514/255, 506, 514/531, 788; 504/234, 261, 347; 540/531; 546/243

[56] References Cited

U.S. PATENT DOCUMENTS

| | | | |
|---|---|---|---|
| 5,071,463 | 12/1991 | Narayanan et al. | 71/79 |
| 5,156,666 | 10/1992 | Narayanan et al. | 71/79 |

OTHER PUBLICATIONS

Derwent 380785-C (1968).

*Primary Examiner*—Peter O'Sullivan
*Attorney, Agent, or Firm*—Jules E. Goldberg; Marilyn J. Maue; Joshua J. Ward

[57] ABSTRACT

A solvent for producing emulsifiable concentrates from agriculturally active chemicals which are insoluble in water comprises an alkoxyalkyl lactam such as butoxy propyl pyrrolidone. An agriculturally active chemical and the alkoxyalkyl lactam are admixed optionally with co-solvents, emulsifiers and surfactants to produce a stable emulsifiable concentrate. The concentrate is dilutable with water at the point of use to produce either macro or micro emulsions which are themselves stable to assure even application.

26 Claims, No Drawings

000
ALKOXYALKYL LACTAMS AS SOLVENTS FOR MACRO AND MICROEMULSIONS

TECHNICAL FIELD

This invention relates to alkoxyalkyl lactams and more particularly to the use of alkoxyalkyl pyrrolidones as solvents for producing emulsifiable concentrates and microemulsions of difficult to dissolve agricultural chemicals.

BACKGROUND OF THE INVENTION

Agricultural chemicals are most preferably applied in the form of aqueous emulsions, solutions or suspensions. Occasionally, they may be applied in powder form where the active ingredient is absorbed onto or mixed with a finely divided inert carrier material, such as china clay or the like. However, such powder composition are subject to wind drift and consequently liquid formulations are preferred.

One problem with liquid formulations is that chemicals having agricultural activity often exhibit extremely poor solubility in water. Consequently, such chemicals are typically dissolved either in organic solvents or utilized in the form of emulsions or suspensions. The use of organic solvents presents particular disadvantages. For example, such solvents may exhibit toxicity or side effects which may be adverse to the effect of the agricultural chemical itself or to the fruit or vegetable produced in the particular agricultural use. This toxicity may also present difficulty with respect to handling and application procedures. Moreover, many organic solvents which have been used in the past, even those exhibiting relatively low toxicities, are not biodegradable and thus remain as a pollutant.

When attempting to provide emulsion or suspension formulations, difficulties are encountered with respect to providing a high concentration of the agriculturally active ingredient, as when such agriculturally active chemicals are formulated into an emulsion, it is difficult to maintain the emulsive state. This make it difficult to maintain a uniform formulation, particular when the formulation is diluted with water for application which may result in uneven application and thus, haphazard results.

The agriculturally active ingredient is typically mixed with one or more of a variety of conventional solvents and an emulsifying agent to form a concentrate which may be an emulsion, a suspension or a solution. The concentrate is then stored until transported to the site of use or may simply be transported and stored at the site of use. In any event, the concentrate normally will undergo some period of storage until it is ready for use. Understandably, it is most desirable to be able to transport the agriculturally active ingredient at the highest concentration possible so as to minimize the volume of material needed for transport. However, at the use site, it is normally not feasible to admix ingredients together or to process them other than to dilute the concentrate with water. Accordingly, it is important that the concentrate emulsify easily, i.e., exhibit good "bloom", upon the addition of water Once made, it is often necessary to store the diluted concentrate for extended periods of time until application. Thus, it is important that the diluted form of the concentrate exhibit good stability with respect to the uniformity of the emulsion and to avoid precipitation of the active ingredients. If non-uniformity or precipitation occurs in the diluted form, this non-uniformity will result in the non-uniform application of alternately high and low concentration formulation.

It is also desirable to increase the efficacy of a given agricultural compound relative to its loading content. It has been theorized that microemulsions can improve the efficacy of agriculturally active compounds relative to equivalent levels of the same compounds in a macro emulsion composition. See Skelton, P. R., Munk B. H., and Collins, H. M., "Formulation of Pesticide Microemulsions" *Pesticide Formulations and Application Systems: 8th Volume ASTM STP* 980, D. A. Hovde and G. B. Beestman, Eds, American Society for Testing and Materials, Philadelphia, 1988. Microemulsion means an oil in water or water in oil, transparent thermodynamically stable dispersion of two or more immiscible liquids wherein the dispersed phase consists of small droplets with diameters in the range of about 10 to 100 millimicrons. Such microemulsions are clear and contain at least 80% by weight water. Clear or transparent as applied to a microemulsion means that the composition appears as a single phase without any particulate or colloidal material or a second phase being present when viewed by the naked eye.

Most of the agricultural chemicals are substantially insoluble or insoluble which means that for all practical purposes, the solubility of the compound in water is insufficient to make the compound practically usable in an agricultural end use without some modification either to increase the solubility or dispersability in water, so as to increase the compound's bio-availability or avoid the use of excessively large volumes of solvent.

Agriculturally active chemicals or ingredients means compounds or mixtures thereof which can be used as agricultural fertilizers, nutrients, plant growth accelerants, herbicides, plant growth controlling chemicals and chemicals which are effective in killing plants, insects, micro-organisms, fungi, bacteria and the like which are commonly referred to as insecticides, bactericides, fungicides, nematocides, fumigants, synergists, i.e., compounds which when used in conjunction with other agriculturally active chemicals enhance their activities and the like as well as any other chemicals having properties which are suitable for agricultural uses in terms of application to plants or domestic uses for controlling insects and pests.

To produce emulsifiable concentrates and micro emulsions, it has been proposed to use $C_1$-$C_4$ lower alkyl pyrrolidones such as described in South African Patent Application No. 695,393 filed Jul. 25, 1969. Additional compounds which provide emulsion stability on dilution are described in U.S. Pat. Nos 5,071,463 and 5,156,666 assigned to the ISP Investments, Inc., the common assignee herewith. While such compounds may be acceptable for producing compositions which deliver effective amounts of an insoluble agriculturally active compound with improved. stability with respect to the emulsion, the search continues for other compounds which may be usable for producing stable emulsifiable concentrates and/or microemulsions of such substantially insoluble compositions.

SUMMARY OF THE INVENTION

It is an object of the present invention to provide a composition suitable for producing a stable emulsifiable concentrate of an agriculturally active chemical which is substantially insoluble in water.

It is another object of the present invention to provide a composition which provides a microemulsion of an agriculturally active. chemical which is substantially insoluble in water.

These and other objects of the present invention are achieved by providing an alkoxyalkyl lactam as a solvent for producing macro and micro emulsions of agriculturally active chemicals which are substantially insoluble in water.

More particularly, we have discovered a solvent for producing highly stable concentrate compositions comprising a water insoluble agriculturally active ingredient, and an alkoxyalkyl lactam solvent having the following formula I:

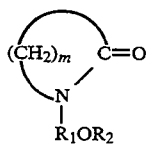

where m=3-5, $R_1$ is an alkylene group having 1-6 carbon atoms, and $R_2$ is a $C_1$-$C_{20}$ alkyl.

More particularly, the solvent is an alkoxyalkyl pyrrolidone of the following formula II:

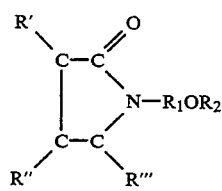

where $R_1$ is an alkylene group having 1 to 6 carbon atoms and $R_2$ is an alkyl, having from 1 to 20 carbon atoms, R', R" and R'" being H or lower alkyl The above solvent is preferably combined with a surfactant and optionally, a hydrophobic solvent and/or co-solvents, to produce emulsifiable concentrates with high loadings which are dilutable for forming emulsions. In one embodiment of the invention, an admixture of the agriculturally active chemical, a surfactant and the solvent of formula I or II is used which is added to water and mixed to produce a micro-emulsion. These are quite stable, both before and after dilution, and allow even application after dilution of the essentially water insoluble agriculturally active compounds in uniform fashion with maximum effectiveness.

DETAILED DESCRIPTION OF THE INVENTION

The solvents of the invention are alkoxyalkyl lactams and more particularly alkoxyalkyl pyrrolidones which are made by a three step process involving the reaction of acrylonitrile with $C_2$ to $C_{20}$ alcohol to produce the alkoxynitrile, followed by hydrogenation to the corresponding amine, and, conversion to the alkoxyalkyl lactam by the reaction of the amine with alkyl lactone.

More particularly, the solvent of the invention comprises an alkoxyalkyl lactam having the following formula I:

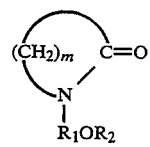

where m=3-5, $R_1$ is an alkylene group having 1-6 carbon atoms, and $R_2$ is a $C_1$-$C_{20}$ alkyl.

More particularly, the solvent is an alkoxy pyrrolidone of the following formula II:

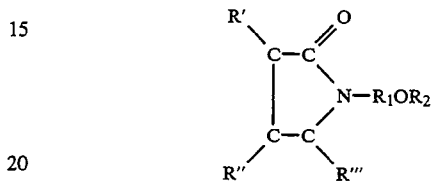

where $R_1$ is an alkylene group having 1 to 6 carbon atoms and $R_2$ is an alkyl, having from 1 to 20 carbon atoms, R', R" and R'" being H or lower alkyl The inventive solvents are particularly useful in providing emulsifiable concentrates and/or microemulsions from agriculturally active chemicals which are substantially insoluble in water, including insecticides, herbicides, fungicides, fumigants, growth regulators, repellents, rodenticides, etc. specifically, those compounds identified as being substantially insoluble in water in U.S. Pat. No. 5,156,666 are suitable for use with the present invention.

Specific alkoxyalkyl solvents such as hexoxymethyl pyrrolidone and octoxymethyl pyrrolidone may be made by the reaction of the corresponding alcohol with either hydroxymethyl pyrrolidone or chloromethyl pyrrolidone. Other alkoxyalkyl solvents such as butoxypropyl pyrrolidone and octoxypropyl pyrrolidone are made by the reaction of acrylonitrile with either butyl or octyl alcohol to form the alkoxypropionitrile followed by hydrogenation to the corresponding amine, and in the final step, conversion to the pyrrolidone by the reaction of the amine with butyrolactone.

EXAMPLE 1—Preparation of Butoxypropionitrile

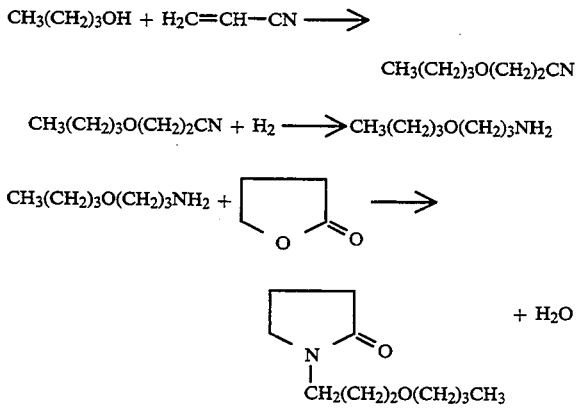

A mixture of 148 grams (2.0 moles) of n-butanol and 2.0 grams of 40% benzyltrimethylammonium hydroxide (Triton B) is combined in a 1 liter 4-neck round bottom flask stirred at reflux while 106 grams (2.0 moles) of acrylonitrile is added at a rate such that the temperature does not exceed 45° C. The mixture is stirred an hour after all the acrylonitrile has been added, made acidic with acetic acid, and fractionated under vacuum through a Vigreux column. The product boils at 75° C./2 mm (literature value: 98° C./20 mm). The product totalled 188.0 grams of 99.0% pure material which constituted a 74.0% yield. The density of the product was determined to be 0.93 grams/ml. The nuclear magnetic resonance and infrared spectra were obtained and were determined to be consistent with the expected structure of the product.

EXAMPLE 2—Preparation of butoxypropylamine

The previously prepared butoxypropionitrile (224.8 grams) was combined with Raney nickel (20 grams of 50/50 mixture with water) in a 1-liter stainless steel autoclave along with a premixed ethanol/ammonium hydroxide solution (37.5 grams of ammonium hydroxide and 212.5 grams of ethanol). The addition of the ammonium hydroxide limits the reaction that leads to the formation of by-product dibutoxypropylamine. After purging with nitrogen, the reactor was pressurized with 500 psi of hydrogen and heated to 60° C. After 20 hours at this temperature, the reactor was cooled to room temperature and the product discharged. The product was filtered to remove the Raney nickel and then distilled using a simple Vigreux column to extract the butoxypropylamine. The distillation produced a yield of about 79.5% of product and 18.3% of the secondary amine.

EXAMPLE 3—Preparation of Butoxypropyl Pyrrolidone.

360 grams of butoxypropylamine (2.75 moles) and 250 grams of butyrolactone (3.0 moles) were charged to a 1-liter stainless steel autoclave. After purging, the mixture was heated to 275° C. for six hours. The reactor was then cooled and the product discharged. The product was distilled with a simple Vigreux column, initially at atmospheric pressure to remove by-product water and then under vacuum (<1 mm) to recover the product. Butoxypropyl Pyrrolidone distills at about 135° C. to 145° C. under these conditions. The recovery was 391.2 grams of >98% pure Butoxypropyl Pyrrolidone.

EXAMPLE 4—Preparation of Octoxypropyl Pyrrolidone

An analogous reaction was carried out to prepare octoxypropyl pyrrolidone from 335.4 grams of octoxypropylamine and 168.7 grams of butyrolactone. As before, the reaction was carried out in a 1-liter stainless steel autoclave at 275° C. for six hours. The crude product (502 grams) was then distilled at atmospheric pressure to remove water (26.0 grams) and then under vacuum to recover the octoxypropyl pyrrolidone. The product distilled at 185° C. at <1 mm pressure. Recovery was 443.8 grams of distilled product (98.0% purity) with 15.0 grams of pot residue. The product had an infrared and nuclear magnetic resonance spectrum consistent with the product.

Compounds isomeric with the alkoxyalkyl pyrrolidones described above may be obtained by an alternate route. For example, either of the following reactions will produce hexoxymethyl pyrrolidone, an isomer of butoxypropyl pyrrolidone.

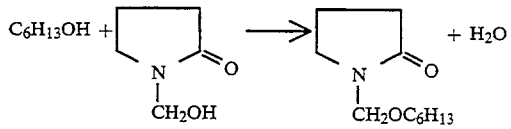

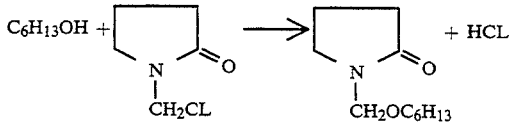

The preparation of octoxymethyl pyrrolidone can be carried out in an exactly analogous manner using 1-octanol instead of 1-hexanol.

EXAMPLE 5—Preparation of Hexoxymethyl Pyrrolidone

A 500 ml round bottom flask equipped with an overhead stirrer, thermocouple with temperature controller, condenser with Dean-Stark apparatus and nitrogen inlet was charged with:
115 grams (1 mole) of hydroxymethyl pyrrolidone;
102 grams (1 mole) of 1-hexanol; and
12 drops of concentrated sulfuric acid.

The reaction mixture was stirred and the temperature was raised in increments from 150° C. to 175° C. and eventually to 195° C. Approximately eight milliliters of water were collected in the Dean-Stark apparatus but it is believed that a significant amount was carried out by the nitrogen stream. The product was recovered and analyzed by gas chromatography. In addition to the major peak which was believed to be the desired product, two other significant peaks were evident. One of these was determined by spiking experiments to be methylene bis-pyrrolidone which arises from the self-condensation of the hydroxymethyl pyrrolidone followed by loss of formaldehyde. The other peak is believed to indicate dihexyl ether which aries from the condensation of 1-hexanol with itself. Distillation using a simple Vigreux column did not separate these peaks completely and the product obtained by distillation at 124° C. (<1 mm) was found to be 85.2% pure hexoxymethyl pyrrolidone.

EXAMPLE 6—Preparation of Hexoxymethyl Pyrrolidone

A charge was made to a 1-liter round bottom flask equipped with an overhead stirrer, thermocouple with controller, condenser and nitrogen inlet as follows:
112 grams (1 mole) of 1-hexanol;
200 ml of toluene; and
52.5 grams of sodium carbonate.

These materials were stirred and heated to 70° C. and then 133.5 grams of chloromethyl pyrrolidone was added dropwise. This led to extensive foaming due to the evolution of carbon dioxide from the carbonate. After completion of the addition of the chloromethyl pyrrolidone, the mixture was stirred at 70° C. for an hour. The reaction product was then filtered to remove the solid, believed to be sodium chloride mixed with excess sodium carbonate and bicarbonate. The toluene was then stripped off in an atmospheric distillation and the product recovered by a vacuum distillation.

Alkoxymethyl and alkoxyethyl pyrrolidones have proven to be effective as surfactants as well as solvents.

In particular, these materials have been formulated as emulsifiable concentrates and microemulsions with various water insoluble agriculturally active chemicals (hereinafter "AAC's") and suitable surfactant/emulsifier systems, optionally in combination with co-solvents, such as polar solvents, hydrophobic solvents and mixtures thereof. Typically, the co-solvents are added to increase or blend the properties of polar and hydrophobic solvents, the ratio and use of such co-solvents determined relative to the choice of agriculturally active chemical. However, the alkoxy alkyl lactam solvents of the invention may be used without any co-solvents.

With the present invention, it is possible to obtain concentrates with agriculturally active chemical concentrations in excess of 5 weight percent which form a stable emulsion upon dilution with water. Depending on the selected AAC, the concentrate may contain from 5-25 percent before dilution.

Examples of appropriate hydrophobic solvents include alkylpyrrolidones having an alkyl portion containing from 6 to 14 carbon atom, e.g., octylpyrrolidone, dodecylpyrrolidone, or N-(2'-ethylhexyl-pyrrolidone), alkyl gamma-butyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. Preferred 6 to 14 carbon alkyl portions are composed of straight chains. Branched or cyclic alkyl portions may also be used. N-ocyl or N-dodecyl pyrrolidone are preferred.

Preferred polar type co-solvents are selected from pyrrolidones having the formula

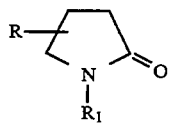

where R is hydrogen or lower alkyl and $R_1$ is lower alkyl, cyclic lactones, lower alkyl cyclic carbonates, lower alkyl imidazolone, lower alkylamides of formic and acetic acid, and lower alkyl sulfoxides, wherein lower alkyl is an alkyl group having from 1 to 4 carbon atoms. N-methyl pyrrolidone is preferred.

Also suitable as a hydrophobic co-solvent are aromatic petroleum oils including those which are commercially available distillates from crude oils having an average boiling point greater than 200° C. Typical of such materials are those sold under the trademarks Exxon 200 or Texaco 400. Of course, such aromatics should be approved for use as a carrier for agriculturally active chemicals.

The composition of the aromatic petroleum oil is generally, heavy aromatic solvent naphtha about 60%, middle distillate solvent extractant about 40%.

Normally, these oils contain predominantly the $C_9$–$C_{15}$ aromatic hydrocabrons and primarily the $C_{10}$–$C_{12}$ hydrocarbons having a flash point of about 203° F.

Another co-solvent usable in the invention is an N, N-dimethyl amide of a carboxylic acid having at least six carbon atoms in the carboxyl component. Preferably, the amount of the amide is from about 15 to 45 weight percent, and most preferable from about 25 to 35 weight percent. Also, a mixture of these amides may be used. Typical of the amides which may be used are:

N, N-Dimethyl Caproamide (N, N-Dimethyl hexamide); N, N-Dimethyl Caprylamide (N, N-Dimethyl octanamide); N, N-Dimethyl Capramide (N, N-Dimethyl decanamide); N, N-Dimethyl lauramide (N, N-Dimethyl dodecanamide); N, N-Dimethyl Myristamide (N, N-tetradecanamide). These compounds are sold under the trademarks Halcomide by CP Hall.

In the inventive composition, the amount of total solvent, inventive solvent plus co-solvent(s), is in the range from about 40 to 90%. The co-solvent(s) may comprise from 0–80% of the inventive composition.

The inventive composition also contains one or more additional emulsifier(s) or surfactant(s) which is generally selected on a case by case basis in order to optimize solubility and stability of the emulsion. Typically, such emulsifiers include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants may be used as the emulsifier and include phosphate esters, and their salts, alkyl sulfonamides, salts of sulfated nonylphenoxypoly(ethyleneoxy) ethanol, salts of alkylbenzene sulfonates, salts of alkylnapthalene sulfonate, and sulfonated aliphatic polyesters and their salts. Also suitable are complex phosphate esters of non-ionic surfactants of the ethylene oxide type which are mixtures of dieters of phosphoric acid. (See, for example, McCutcheon's, *Emulsifiers and Detergents* (1989), published by McCutcheon's Division of M. C. Publishing Co., Glen Rock, N.J.) Generally, the amount of emulsifier (surfactant) is from about 1 to 25% based on the total weight of the composition.

With the present invention, it is possible to obtain concentrates with agriculturally active chemical ("ACC") concentrations in excess of 5 weight percent which form a stable emulsion upon being diluted with water. Depending on the particular agriculturally active chemical, the concentration of the AAC is from about 5 to 25% based on the total weight of the composition before dilution. In particular, the emulsified concentrate in accordance with the present invention can be diluted to final use concentrations in the range from about 10 ppm to 2 percent, depending on the specific AAC, without any adverse effects, and specifically, precipitation of the AAC from the solution.

Emulsifiable concentrates were made with the highest possible loading of AAC'S with two compounds of formula II; IIa, where $R_1$ was $C_3H_6$ and $R_2$ was $C_4H_9$ (butoxypropryl pyrrolidone), and IIb where $R_1$ was $C_3H_6$ and $R_2$ was $C_8H_{17}$ (octoxy propyl pyrollidone) In both compounds, R', R" and R'" were H. N-methyl pyrrolidone (NMP), N-octyl pyrrolidone (NOP), N-dodecyl pyrrolidone (NDDP) and/or Halcomide were used as co-solvents. Exxon aromatic 200 was used as another hydrophobic solvent. Additionally, Gafac RE 610, Silwet L 7607 and/or Igepal CO630 were used as surfactants. The active ingredients were pendimethaiin, carbaryl, triforine and thidiazuron. The performance of the emulsifiable concentrates were evaluated in terms of freeze/thaw stability, active ingredient loading, emulsion stability on standing after dilution, crystal growth and solid separation after dilution, both on standing and stirring, via microscopic examination.

EXPERIMENT 7—Determination of solubility of AAC

A weighted quantity of an active ingredient was stirred with 10 grams of a solvent in an automatic orbital shaker for 30 minutes, starting with 0.1 to 1 grams of active ingredient depending upon its solubility. Incremental amounts of active ingredient (0.1 gram) were added until there was no dissolution after stirring for 30 minutes to obtain the highest limit of solubility. Incremental amounts of solvent (0.1 gram) were then added until a solution was again obtained, establishing the lower end of solubility. All determinations were made at ambient conditions, approximately 20° to 25° C. Results from these tests are shown in Table I, which establishes that the alkoxy alkyl solvents are comparable to or superior to the other tested solvents.

TABLE I

RELATIVE SOLUBILITIES OF ACC'S

| ACC | NMP | NOP | HALCOMIDE 8-10 | NDDP | IIa | IIb |
|---|---|---|---|---|---|---|
| Atrazine | 20–24 | 12–16 | 6–9 | 9–10 | 9.0–11 | 9–11 |
| Triforine | 34–36 | 13–18 | 6–8 | 7–10 | 13.0 | 9–11 |
| Thidiazuron | 13–15 | 21–23 | 5–6 | 13–16 | 21–25 | 13–15 |
| Carbaryl | 45–48 | 24–32 | 20–24 | 16–20 | 27–30 | 16–18 |
| Pendimethalin | 66–68 | 42–45 | 48–49 | >44 | 39–41 | 32–34 |

EXPERIMENT 8—Preparation of emulsible concentrate formulations

Formulations were prepared by weighing and mixing an exact proportion of ingredients. An active ingredient was dissolved completely in a measured solvent amount to which a wetting agent or emulsifying agent was added. Contents were mixed in an automatic orbital shaker until the active ingredient was dissolved completely, typically in 30 minutes. Table II lists the percent composition of formulations made. Formula III has no alkoxy alkyl lactam solvent, formulas XIV and XV have no co-solvents or hydrophobic solvents.

TABLE II

% COMPOSITIONS OF FORMULATIONS

| COMPONENT | I | II | III | IV | V |
|---|---|---|---|---|---|
| N-Methyl Pyrrolidone | 10 | 0 | 10 | 10 | 32 |
| Halcomide (M-8-10) | 0 | 0 | 0 | 0 | 0 |
| N-Octyl Pyrrolidone | 0 | 39 | 70 | 0 | 0 |
| N-Dodecyl Pyrrolidone | 0 | 0 | 0 | 0 | 0 |
| Butoxy-Propyl Pyrrolidone (IIa) | 70 | 39 | 0 | 50 | 8 |
| Octoxy-Propyl Pyrrolidone (IIb) | 0 | 0 | 0 | 0 | 8 |
| Aro-Exxon 200 | 0 | 0 | 0 | 20 | 12 |
| Gafac RE-610 | 5 | 5.5 | 5 | 5 | 15 |
| Silwet L-7607 | 5 | 5.5 | 5 | 5 | 0 |
| Igepal C0630 | 0 | 0 | 0 | 0 | 0 |
| AACS: | | | | | |
| Pendimethalin | 0 | 0 | 0 | 0 | 25 |
| Carbaryl | 10 | 11.0 | 10 | 10 | 0 |
| Triforine | 0 | 0 | 0 | 0 | 0 |
| Thidiazuron | 0 | 0 | 0 | 0 | 0 |
| TOTAL | 100 | 100 | 100 | 100 | 100 |
| Solubility | S | S | S | S | S |

"S" Means Complete Solubility

| COMPONENT | VI | VII | VIII | IX | X |
|---|---|---|---|---|---|
| N-Methyl Pyrrolidone | 16 | 16 | 36 | 36 | 36 |
| Halcomide (M-8-10) | 0 | 0 | 0 | 0 | 14 |
| N-Octyl Pyrrolidone | 0 | 0 | 0 | 14 | 0 |
| N-Dodecyl Pyrrolidone | 0 | 0 | 0 | 0 | 0 |
| Butoxy-Propyl Pyrrolidone | 32 | 24 | 27 | 13 | 13 |
| Octoxy-Propyl Pyrrolidone | 0 | 0 | 0 | 0 | 0 |
| Aro-Exxon 200 | 12 | 12 | 27 | 27 | 27 |
| Gafac RE-610 | 15 | 15 | 5 | 5 | 5 |
| Silwet L-7607 | 0 | 0 | 0 | 0 | 0 |
| Igepal C0630 | 0 | 0 | 0 | 0 | 0 |
| AACS: | | | | | |
| Pendimethalin | 25 | 25 | 0 | 0 | 0 |
| Carbaryl | 0 | 0 | 0 | 0 | 0 |
| Triforine | 0 | 0 | 0 | 0 | 0 |
| Thidiazuron | 0 | 0 | 0 | 0 | 0 |
| TOTAL | 100 | 100 | 100 | 100 | 100 |
| Solubility | S | S | S | S | S |

"S" Means Complete Solubility

| COMPONENT | XI | XII | XIII | XIV | XV |
|---|---|---|---|---|---|
| N-Methyl Pyrrolidone | 24 | 24 | 0 | 0 | 0 |
| Halcomide (M-8-10) | 0 | 0 | 37.5 | 0 | 0 |
| N-Octyl Pyrrolidone | 0 | 0 | 0 | 0 | 0 |
| N-Dodecyl Pyrrolidone | 0 | 0 | 0 | 0 | 0 |
| Butoxy-Propyl Pyrrolidone | 32 | 16 | 40 | 40 | 40 |
| Octoxy-Propyl Pyrrolidone | 0 | 16 | 0 | 37.5 | 37.5 |
| Aro-Exxon 200 | 24 | 24 | 0 | 0 | 0 |
| Gafac RE-610 | 5 | 5 | 10 | 10 | 0 |
| Silwet L-7607 | 5 | 5 | 0 | 0 | 0 |
| Igepal C0630 | 0 | 0 | 0 | 0 | 0 |
| AACS: | | | | | |
| Pendimethalin | 0 | 0 | 0 | 0 | 0 |
| Carbaryl | 0 | 0 | 0 | 0 | 0 |
| Triforine | 10 | 10 | 0 | 0 | 0 |
| Thidiazuron | 0 | 0 | 10 | 10 | 10 |
| TOTAL | 100 | 100 | 100 | 100 | 100 |
| Solubility | S | S | S | S | S |

"S" Means Complete Solubility

EXAMPLE 9—Evaluation of emulsion stability

A 0.5 to 2.5 gram aliquot of an emulsifiable concentrate prepared in example 8 was pipetted into a Nessler tube filed with 47.5 to 49.5 grams of WHO water (342 ppm hardness expressed as $CaCO_3$ equivalent). The initial bloom was observed at zero time and the quality of the bloom graded by visual appearance. The Nessler tube was then inverted 20 times and both the bloom and stability evaluated by volume or height of the sediment (cream/ppt/oil). Similar measurements were made at intervals of 1, 2, 4 and 24 hours. The results are shown in Table III. The ratings on bloom were excellent (thick emulsion cloud with no separation), good (emulsion cloud may be thin or may exhibit trailing, small number of oil droplets within the cloud) and poor (many oil droplets in cloud, some droplets may separate from the cloud). The diluted concentrate was considered stable if the final dilutions after mixing (20 inversions) exhibited 2 mm or less cream and no oil in one hour. All the formulations using the inventive solvents were stable.

TABLE III

Results of Emulsion Stability on Standing (Nessler Tube)

| | FORMULA NO. | | | | | | | |
|---|---|---|---|---|---|---|---|---|
| | I | II | III | IV | V | VI | VII | VIII |
| Dilution | 2.5 g/50 g 342 ppm hardness water | | | | | | | |
| Bloom zero Time | Very Good | Good | No Emulsion | No Emulsion | Excellent | Excellent | Excellent | Good |
| After 20 Inversions | Very Good | Very Good | Fair | Good | Excellent | Excellent | Excellent | Excellent |
| Solids/[1] Cream/oil mm | T  B | T  B | T  B | T  B | T  B | T  B | T  B | T  B |
| Time: | | | | | | | | |
| 0 h | 0  0 | 0  0 | 0  0 | 0  0 | 0  0 | 0  0 | 0  0 | 0  0.5 |
| 1 h | 0  0 | 0  0 | 0  0 | 0  0 | 0  2 | 0  0 | 0  0.05 | 0  TR |
| 2 h | 10  0 | 0  0 | 0  2 | 4  0 | 0  2 | 0  0.5 | 0  2 | 0  1 |
| 4 h | 10  0 | 0  0 | 4  3 | 15  0 | 0  3 | 0  0.5 | 0  3 | 0  1 |
| 24 h | 10  0 | 0  0 | 8  7 | 15  0 | 0  4 | 0  0.5 | 0  3 | 0  1 |
| Crystals at 25OX[2] | | * | | 0 | 0 | 0 | 0 | 0 |
| Filtration through Screens after 24 h standing and 20 inversions[3] | | | | | | | | |
| 60 Mesh | 0 | 0 | 0 | 0 | + | 0 | + | 0 |
| 100 " | + | 0 | 0 | 0 | + | 0 | + | 0 |
| 250 " | + | + | + | 0 | + | + | + | + |

| | FORMULA NO. | | | | | | |
|---|---|---|---|---|---|---|---|
| | IX | X | XI | XII | XIII | XIV | XV |
| Dilution | 2.5 g/50 g 342 ppm hardness water | | | | | | |
| Bloom Zero Time | Good | Good | No Emulsion | Good | No Emulsion | No Emulsion | Excellent |
| After 20 Inversions | Good | Good | Good | Good | Good | Good | Excellent |
| Solids/Cream/oil mm | T  B | T  B | T  B | T  B | T  B | T  B | T  B |
| Time: | | | | | | | |
| 0 h | 0  0 | 0  0 | 0  0 | 0  0 | 0  0 | 0  0 | 0  0 |
| 1 h | 0  0 | 0  0 | 0  0 | 0  1 | 0  TR | 0  0 | 0  0 |
| 2 h | 0  0 | 0  0 | 0  3 | 0  2 | 0  9 | 0  0 | 0  0 |
| 4 h | 0  0 | 0  0 | 0  3 | 0  3 | 0  0 | 0  0 | 0  5 |
| 24 h | 4  4 | 5  35 | 0  4 | 0  5 | 0  10 | 0  7 | 0  7 |
| Crystals at 25OX | — | — | — | — | 0 | — | 0 |
| Filtration through Screens after 24 h standing and 20 inversions | | | | | | | |
| 60 Mesh | ++ | + | ++ | 0 | 0 | 0 | ++ |
| 100 " | + | + | + | 0 | 0 | 0 | + |
| 250 " | + | + | + | + | + | 0 | + |

[1]T: Top; B: Bottom; TR means trace
[2]0 = no crystals; * = 0–50 crystals;  = 50–100 crystals * = >100 crystals
[3]0 means no sediments; + means more than a trace, ++ means 1–5% sediments.

EXAMPLE 10—Crystal Growth

Samples were evaluated for precipitation of active ingredient (crystal growth) over varying time periods. A diluted sample was placed in a 100 ml beaker and stirred continuously. Aliquots were removed at 0, 2, 4, 6, and 24 hour intervals and examined under 250× magnification using a 40 by 30 grid on a 2 by 2 cm slide. The number of crystals in 10 different grids were counted and averaged. If no crystals were found, second and third aliquots were examined. The remaining portion of the diluted sample was then passed through U.S. standard screens having 60, 100 and 250 mesh. The amount of sediment retained was recorded. The diluted sample was then allowed to stand without stirring for 24 hours and then inverted 20 times. An aliquot was then examined for crystals. The remaining portion was passed through the screens and retained sediments recorded. The results are shown in Table IV, establishing the satisfactory performance using the inventive solvents.

TABLE IV

Microscopic Observation of Crystal Growth from formulations on Dilution and Stirring[1]

| | FORMULA NO. | | | | | | | |
|---|---|---|---|---|---|---|---|---|
| | I | II | III | IV | V | VI | VII | VIII |
| Dilution Time: | 2.5 g/50 g 342 ppm hardness water | | | | | | | |
| 0 h | 0 | * | * | * | 0 | * | 0 | 0/* |
| 1 h | 0 | * | * | * | 0 | 0 | 0 | 0 |
| 2 h | 0 | * | * | * | 0 | 0 | 0 | 0 |
| 4 h | 0 | * | * | * | 0 | 0 | 0 | 0 |
| 24 h | * | * | * | * | 0 | 0 | * | 0 |
| After 24 h, filtering through screens | | | | | | | | |
| 60 Mesh | 0 | 0 | 0 | + | 0 | 0 | 0 | 0 |
| 100 " | 0 | + | 0 | + | 0 | 0 | 0 | 0 |
| 250 " | 0 | + | ++ | ++ | + | + | 0 | 0 |

| | FORMULA NO. | | | | | | |
|---|---|---|---|---|---|---|---|
| | IX | X | XI | XII | XIII | XIV | XV |
| Dilution Time: | 2.5 g/50 g 342 ppm hardness water | | | | | | |
| 0 h | ** | ** | * | 0 | 0/* | *** | *** |
| 1 h | * | ** | * | 0 | * | ** | — |
| 2 h | * | ** | 0 | 0 | 0 | — | ** |
| 4 h | * | ** | 0 | 0 | 0 | 0 | 0 |
| 24 h | * | * | 0 | 0 | 0 | * | * |
| After 24 h, filtering through screens | | | | | | | |
| 60 Mesh | ++ | ++ | 0 | ++ | 0 | — | 0 |
| 100 " | 0 | ++ | 0 | + | 0 | — | + |
| 250 " | 0 | ++ | 0 | + | + | — | + |

[1]See Table III for notations.

EXAMPLE 11—Freeze thaw stability

The concentrates of Table II were stored for 24 hours at $-10°$ C. to 5° C., thawed to room temperature and then heated to 55° C. and held for 24 hours. The alternative cold and hot condition was repeated for three cycles with any separation during storage recorded. A concentrate is considered stable if there is no substantial separation after three cycles. All of the formulations were found to exhibit good freeze thaw stability.

EXAMPLE 12—Preparation of microemulsions

Four microemulsions were prepared from admixtures using butoxy propyl pyrrolidone as shown in Table V. The admixtures were prepared and then added to water, with mixing.

TABLE V

MICROEMULSION FORMULATIONS

| | ADMIXTURE: | | | |
|---|---|---|---|---|
| | XVI | XVII | XVIII | XIX |
| Butoxypropyl Pyrrolidone | 5 | 0.2 | 5 | 0.1 |
| N-methylpyrrolidone | 0 | 0 | 0 | 0.2 |
| Sodium dodecyl sulfate | 2 | 0 | 0 | 0 |
| Igepal CO 630 | 0 | 0.1 | 0 | 0.6 |
| Gafar RE 610 | 0 | 0.2 | 0 | 0 |
| Pegol L 31 | 0 | 0 | 0 | 0.1 |
| Sodium dodecyl benzene sulfonate | 0 | 0 | 2 | 0 |
| Carbaryl | 0.2 | 0 | 0.2 | 0 |
| Permethrin | 0 | 0.1 | 0 | 0.3 |
| Added to Water | 92.8 | 99.4 | 92.8 | 98.7 |
| Total | 100.0 | 100.0 | 100.0 | 100.0 |

The above compositions formed microemulsions which remained clear, after observing for up to 2 weeks. The formulations using the inventive solvent thus provide stable microemulsions.

Utilizing the inventive alkoxyalkyl lactam solvents, stable emulsifying concentrates of agriculturally active chemicals can be prepared which exhibit good stability after dilution with water. Additionally, these solvents promote preparation of microemulsions from admixtures which enhance effectiveness on application. Thus, water insoluble agriculturally active chemicals are provided in a form suitable for aqueous dispersion at the point of use, avoiding organic solvents.

While preferred embodiments of the present invention have been shown and described, it will be understood by those skilled in the art that various changes and modifications could be made without varying from the scope of the present invention.

What is claimed is:

1. A stable emulsifiable concentrate comprising an agriculturally active chemical which is substantially insoluble in water, a surfactant, and a biodegradable alkoxyalkyl lactam solvent having the following formula:

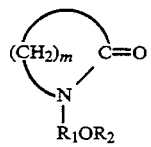

where $m=3-5$, $R_1$ is an alkylene group having 1-6 carbon atoms, and $R_2$ is a $C_1-C_{20}$ alkyl.

2. The emulsifiable concentrate of claim 1 wherein m equals 3.

3. The emulsifiable concentrate of claim 1 wherein the solvent comprises from 10 to 90% of the concentrate.

4. The emulsifiable concentrate of claim 1 wherein the surfactant is selected from the group consisting of ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines.

5. The emulsifiable concentrate of claim 1 wherein the surfactant is present in an amount of from 1–25%.

6. The emulsifiable concentrate of claim 1 further comprising a co-solvent.

7. The emulsifiable concentrate of claim 6 wherein the co-solvent is selected from pyrrolidones having the formula:

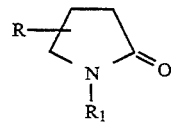

where R is hydrogen or lower alkyl and $R_1$ is lower alkyl, cyclic lactones, lower alkyl cyclic carbonates, lower alkyl imidazolone, lower alkylamides of formic and acetic acid, and lower alkyl sulfoxides, wherein lower alkyl is an alkyl group having from 1 to 4 carbon atoms.

8. The emulsifiable concentrate of claim 6 wherein the co-solvent is N-methlypyrrolidone.

9. The emulsifiable concentrate of claim 6 wherein the co-solvent is a hydrophobic solvent.

10. The emulsifiable concentrate of claim 9 wherein the hydrophobic solvent is selected from the group consisting of octylpyrrolidone, dodecylpyrrolidone, or N-(2'-ethylhexyl-pyrrolidone), alkyl gamma-butyrolactones, alkyl cyclic carbonates and combinations thereof, wherein the alkyl chains contain from 6 to 14 carbon atoms.

11. The emulsifiable concentrate of claim 10 wherein the hydrophobic solvent having 6–14 carbon alkyl portions are composed of straight chains, branched or cyclic alkyl portions.

12. The emulsifiable concentrate of claim 10 wherein the hydrophobic solvent is selected from the group consisting of N-ocyl pyrrolidone, N-dodecylpyrrolidone and combinations thereof.

13. The emulsifiable concentrate of claim 9 wherein the concentration of active ingredient is in excess of about 5 weight percent based on the weight of the total weight of the concentrate.

14. The emulsifiable concentrate of claim 1 wherein the amount of the active ingredient is from 5 to 25% by weight based on the total weight of the concentrate.

15. A composition comprising the emulsifiable concentrate of claim 1 and water wherein the active ingredient is present in an effective amount.

16. The emulsifiable concentrate of claim 1 wherein the agricultural active chemical is selected from the group consisting of insecticides, herbicides, fungicides, fumigants, growth regulators, repellents and rodenticides.

17. A method for treatment of a plant comprising providing the stable emulsifiable concentrate of claim 1, having a herbicide as the selected active ingredient, mixing the concentrate with water wherein the herbicide is present in an effective amount, and applying said composition to said plant or the soil surrounding said plant.

18. A stable emulsifiable concentrate comprising an agriculturally active chemical which is substantially insoluble in water, a surfactant, and a biodegradable alkoxyalkyl pyrrolidone solvent having the following formula:

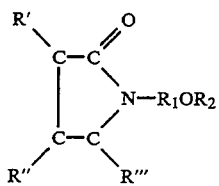

wherein $R_1$ is an alkylene group having 1 to 6 carbon atoms and $R_2$ is an alkyl, having from 1 to 20 carbon atoms, R', R" and R''' being h or lower alkyl.

19. The solvent of claim 18 wherein $R_1$ is $C_3H_6$, $R_2$ is $C_8H_{17}$ and R' R" and R''' are H.

20. The emulsifiable concentrate of claim 18 where in m equals 3.

21. The emulsifiable concentrate of claim 18 wherein the solvent comprises from 10 to 90% of the concentrate.

22. The emulsifiable concentrate of claim 18 wherein the surfactant is selected from the group consisting of ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines, alkyl sulfates, sulfonates, alkyl/aryl sufates, sulfonates, phosphates, ethoxylated version of the sulfates, sulfonates and phosphates.

23. The emulsifiable concentrate of claim wherein the surfactant is present in an amount of from 1-25%.

24. The emulsifiable concentrate of claim 18 further comprising a co-solvent.

25. The emulsifiable concentrate of claim 24 wherein the co-solvent is selected from pyrrolidones having the formula:

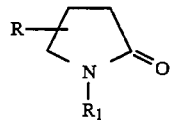

where R is hydrogen or lower alkyl and $R_1$ is lower alkyl, cyclic lactones, lower alkyl cyclic carbonates, lower alkyl imidazolone, lower alkylamides of formic and acetic acid, and lower alkyl sulfoxides, wherein lower alkyl is an alkyl group having from 1 to 4 carbon atoms.

26. The emulsifiable concentrate of claim 24 wherein the co-solvent is N-methlypyrrolidone.

* * * * *